United States Patent
Brunner et al.

(10) Patent No.: US 6,638,619 B1
(45) Date of Patent: Oct. 28, 2003

(54) METHOD FOR PRODUCING A GRANULATE FROM A MELT

(75) Inventors: Melanie Brunner, Mannheim (DE); Rudolf Erich Lorenz, Ludwigshafen (DE); Bernhard Maltry, Obrigheim (DE); Jörg Heilek, Bammental (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 72 days.

(21) Appl. No.: 10/030,432

(22) PCT Filed: Jul. 11, 2000

(86) PCT No.: PCT/EP00/06576

§ 371 (c)(1),
(2), (4) Date: Jan. 10, 2002

(87) PCT Pub. No.: WO01/05495

PCT Pub. Date: Jan. 25, 2001

(30) Foreign Application Priority Data

Jul. 15, 1999 (DE) .......................... 199 33 289

(51) Int. Cl.$^7$ .............. B32B 5/16; B29B 9/00
(52) U.S. Cl. ............... 428/402; 264/5; 264/15; 264/348
(58) Field of Search .................... 428/402; 425/6, 425/10; 264/5, 15, 28, 348

(56) References Cited

U.S. PATENT DOCUMENTS

| | | | | |
|---|---|---|---|---|
| 2,448,072 A | | 11/1949 | Stewart | ................ 223/95 |
| 3,308,217 A | * | 3/1967 | Lowy et al. | |
| 3,721,725 A | * | 3/1973 | Briggs et al. | |
| 4,578,021 A | | 3/1986 | Schermutzki | ................ 425/6 |
| 5,019,302 A | * | 5/1991 | Sparks et al. | |
| 5,389,380 A | * | 2/1995 | Noda et al. | |
| 5,741,519 A | * | 4/1998 | Rosenberg et al. | |
| 5,936,115 A | | 8/1999 | Melder et al. | ............ 560/189 |
| 6,224,639 B1 | | 5/2001 | Weuer et al. | ............ 560/179 |
| 6,413,541 B1 | * | 7/2002 | Shirai et al. | |
| 6,416,786 B1 | * | 7/2002 | Mulye et al. | |

FOREIGN PATENT DOCUMENTS

| DE | 32 09 747 | 9/1983 |
|---|---|---|
| DE | 19637380 | 9/1996 |
| EP | 884097 | 12/1998 |

OTHER PUBLICATIONS

Derwent Abstract; Week 199402, Class D21, AN1994–013829.

* cited by examiner

Primary Examiner—H. Thi Le
(74) Attorney, Agent, or Firm—Keil & Weinkauf

(57) ABSTRACT

A process for the production of tablet-shaped granular material from a melt, in which
(i) a melt is prepared,
(ii) the prepared melt is shaped to droplets,
(iii) the droplets are deposited on a cooling surface, and
(iv) the deposited droplets solidify to give the granular material, wherein the melt comprises an alcohol, and the melt has a melting point of 30° C. or above.

14 Claims, No Drawings

METHOD FOR PRODUCING A GRANULATE FROM A MELT

The present invention relates to a process for the production of granular material from a melt, and to the granular material itself.

Processes for the production of granular materials have already been described in the prior art. However, many of these processes have disadvantages, for example high equipment complexity. This equipment complexity is particularly high if the aim is to produce granular materials having, for example, a tablet-shaped geometry.

DE-C 32 09 747, for example, describes a process for the production of a granular material from a melt in which the crystal content of the melt is of very crucial importance. In order to be able to control this crystal content as well as possible, use is made of a pre-crystallizer, in which the melt has to be enriched with crystal nuclei.

DE-C 196 37 380 discloses the production of neopentyl glycol hydroxypivalate granules. In this process too, the crystal content of the melt is of essential importance. The crystal content is achieved in this process either by adding additional solid to the melt or, as in DE-C 32 09 747, by using a pre-crystallizer. A two-phase mixture having a certain content of crystals has to be produced in this pre-crystallizer. In this case, the equipment complexity is likewise very high since, in addition to the pre-crystallization, measures have to be taken to ensure a certain degree of homogeneity of the 2-phase mixture.

It is an object of the present invention to provide a process which allows the production of a tablet-shaped granular material and which does not have the disadvantages of corresponding processes from the prior art.

We have found that this object is achieved by a process for the production of a tablet-shaped granular material from a melt, in which (i) a melt is prepared,
(ii) the prepared melt is shaped to give droplets,
(iii) the droplets are deposited on a cooling surface, and
(iv) the deposited droplets solidify to give the granular material, wherein the melt comprises an alcohol, and the melt has a melting point of 30° C. or above.

The present invention likewise relates to the tablet-shaped granular material which can be produced by a process in which (i) a melt is prepared,
(ii) the prepared melt is shaped to give droplets,
(iii) the droplets are deposited on a cooling surface, and
(iv) the deposited droplets solidify to give the granular material, wherein the melt comprises an alcohol, and the melt has a melting point of 30° C. or above.

The term "tablet-shaped granular material", as used in the context of the present application, describes a granular material with a circular to oval outline whose underside is flat and whose upper side is flat to convex.

Regarding the alcohol present in the melt, there is generally no restriction so long as the melt comprising the alcohol has a melting point of 30° C. or above, preferably a melting point of 40° C. or above. In particular, the alcohol can be a linear, branched or cyclic substituted or unsubstituted alcohol. Conceivable here are both monools and polyols, which may in turn be monomeric, oligomeric or polymeric.

It is of course also conceivable for the melt to comprise two or more alcohols.

In a preferred embodiment, the present invention relates to a process as described above wherein the alcohol is selected from the group consisting of (a) an alcohol (B) which is prepared by a process which comprises the following stages (I) to (III):
  (I) reaction of at least one alkali or alkaline earth metal hydroxide with at least one alcohol (A) in at least one organic solvent (L) to give a mixture (G-I) comprising at least the alcohol (A), the solvent (L) and an alkoxide (AL);
  (II) reaction of at least one carbonyl compound of the general structure R—CO—R' with at least one alkyne of the general structure R"—C≡C—H and the mixture (G-I) obtained in stage (I) to give a mixture (G-II) comprising at least the alcohol (A), the solvent (L) and an unsaturated alcohol (B);
  (III) distillation of the mixture (G-II) obtained in stage (II) to give the at least one alcohol (B) and a mixture (G-Ill) comprising the solvent (L) and the alcohol (A),
  where the solvent (L) obtained in stage (III) and the alcohol (A) obtained in stage (III) are recycled into stage (I) as a mixture,
(b) an alcohol (C) which is prepared by a process which comprises the following stages (I) to (III'):
  (I) reaction of at least one alkali or alkaline earth metal hydroxide with at least one alcohol (A) in at least one organic solvent (L) to give a mixture (G-I) comprising at least the alcohol (A), the solvent (L) and an alkoxide (AL);
  (II) reaction of at least one carbonyl compound of the general structure R—CO—R' with at least one alkyne of the general structure R"—C≡C—H and the mixture (G-I) obtained in stage (I) to give a mixture (G-II) comprising at least the alcohol (A), the solvent (L) and an unsaturated alcohol (B);
  (II') hydrogenation of at least one unsaturated alcohol (B) in the mixture (G-II) obtained from stage (II) to give a mixture (G-II') comprising at least one hydrogenated alcohol (C), the alcohol (A) and the solvent (L);
  (III') distillation of the mixture (G-II') obtained in stage (II') to give the at least one alcohol (C) and a mixture (G-III') comprising the solvent (L) and the alcohol (A),
  where the solvent (L) obtained in stage (III') and the alcohol (A) obtained in stage (III') are recycled into stage (I) as a mixture, and
(c) a mixture of two or more thereof.

There are no particular restrictions regarding the preparation of the mixture (G-I) in stage (I), which comprises the solvent (L), the alcohol (A) and the alkoxide (AL). It must merely be ensured that (L) and (A) can be added together as starting materials.

In a preferred embodiment, stage (I) is carried out in one or more distillation columns in which the at least one alkoxide is prepared by azeotropic drying. It is possible here, for example, to supply (L) and (A) as a single starting-material stream already in the form of a mixture. However, it is likewise possible to supply (L) and (A) separately and only to combine the streams in the at least one column. It is of course also possible to employ a plurality of suitable solvents (L) and/or a plurality of suitable alcohols (A). It is conceivable here to feed these to the at least one column in a single starting-material stream or in two or more starting-material streams which comprise the respective solvents (L) and/or the respective alcohols (A).

In addition to (L) and (A), an aqueous solution of one or more alkali and/or alkaline earth metal hydroxides in one or more starting-material streams is added as further starting material. The use of alkali and/or alkaline earth metal hydrides and/or alkali and/or alkaline earth metal alkyl compounds is also conceivable in this connection.

If it should be necessary for the purposes of the present invention, the individual starting-material streams can of course be brought to the desired temperature before the pre-mixing. Such preheating is possible in all conceivable processes.

Removal of water by distillation during performance of stage (I) from the at least one alcohol (A) and the at least one alkali and/or alkaline metal hydroxide gives a mixture comprising at least one alkali or alkaline earth metal alkoxide and the at least one organic solvent (L). This mixture is preferably obtained from the still of the column used.

In the further course of performance of stage (I), the excess at least one alcohol (A) is removed from this mixture by distillation. This removal can be carried out either in the same column in which the at least one alkoxide was prepared or in one or more downstream columns. In a preferred embodiment of the present invention, stage (I) is carried out in a single column in which both water and the at least one alcohol (A) are distilled off.

In the present invention, sufficient alcohol (A) is removed so that the mixture resulting after the removal of water and the incomplete removal of the at least one alcohol (A) generally comprises from 0 to 55% by weight of the alcohol (A). Preferably, however, the process is carried out in such a way that the alcohol (A) is not removed quantitatively. Instead, the process is carried out in such a way that the mixture resulting after the removal of water and the incomplete removal of the at least one alcohol (A) comprises from 1 to 55% by weight, preferably from 2 to 10% by weight and particularly preferably in the region of approximately 5% by weight of alcohol (A).

During the removal of water in stage (I), it is conceivable, depending on the selected solvent (L) and alcohol (A), for a certain proportion of (L) and/or (A) to be distilled off together with the water as a multiphase mixture. If this is the case, it is possible in the process according to the invention to feed this removed, multiphase mixture comprising water and (L) and/or (A) to a phase separator and to separate the individual phases. It is thus possible to recycle (L) and/or (A) removed to such an extent as starting material(s) in stage (I). The aqueous phase removed to this extent can also be employed in the process according to the invention, as described below, in a further stage of the process. Alcohols (A) which can be employed in the process according to the invention are, inter alia, primary and secondary alcohols having 4 to 8 carbon atoms, such as n-butanol, isobutanol, n-pentanol, 3-methyl-1-butanol, 2-methyl-1-butanol, 2,2-dimethyl-1-propanol, n-hexanol, 2-ethyl-1-hexanol, 2-butanol, 2-pentanol, 3-pentanol, 2-methyl-3-butanol, 2-methyl-2-butanol or cyclohexanol. Also conceivable are of course compounds of the general structure HO—$CH_2$—$CH_2$—OR, where R is selected in such a way that the respective compound is soluble in the solvent (mixture) used. Particular preference is given here to n-butanol and isobutanol, particularly preferably isobutanol.

The organic solvents (L) used are generally polar aprotic solvents, inter alia aliphatic, cycloaliphatic and/or substituted or unsubstituted aromatic hydrocarbons, for example cyclohexane, benzene, toluene, xylene, cumene or p-diisopropylbenzene, acetals of aldehydes and ketones, symmetrical or asymmetrical dialkyl ethers of ethane or butane, or polyalkylene glycols containing $C_2$— to $C_6$-alkyl radicals. In the process according to the invention, particular preference is given to aromatic hydrocarbons, especially xylene.

Preferred hydroxides in the process according to the invention are alkali metal hydroxides, where KOH is particularly preferred. If the aqueous solution of KOH is used, preference is given to a solution which generally contains from 2 to 60% by weight, preferably from 5 to 50% by weight, particularly preferably from 30 to 35% by weight of KOH.

The above-described mixture, which also comprises a certain proportion of alcohol (A) and solvent (L) and alkoxide (AL), is fed to stage (II) after stage (I). In this stage (II) of the process according to the invention, at least one carbonyl compound of the general structure R—CO—R' is reacted with at least one alkyne of the general structure R"—C≡C—H and the mixture (G-I) obtained in stage (I), giving an alcohol (B).

In a preferred embodiment of the process according to the invention, the mixture (G-I) obtained from stage (I), comprising the solvent (L), the alcohol (A) and alkoxide (AL), is to this end introduced into a suitable reactor, and the at least one alkyne and the at least one carbonyl compound are introduced.

The introduction of alkyne and/or carbonyl compound can take place by any suitable method. For example, it is possible to combine the alkyne and carbonyl compound to give a starting-material stream before introduction into the reactor, and to feed this stream into the reactor. However, it is of course also possible to feed the alkyne and carbonyl compound into the reactor separately from one another as individual starting-material streams.

It is furthermore possible, in the case where the alkyne and carbonyl compound are fed into the reactor separately from one another as individual starting-material streams, first to introduce the alkyne and then the carbonyl compound. It is of course also conceivable first to introduce the alkyne and then, with continued introduction of the alkyne, to add the carbonyl compound and to introduce the alkyne and carbonyl compound in parallel. In a preferred embodiment of the invention, the alkyne and carbonyl compound are introduced simultaneously into the mixture (G-I) from stage (I) as separate starting-material streams in stage (II).

The introduction here can in principle take place batchwise or continuously. The introduction preferably takes place continuously.

Depending on the selected temperature at which the reaction in stage (II) is to take place, it may be appropriate already to bring the individual components to the requisite temperature before feeding into the reactor, which is conceivable in all processes from the prior art. In particular, it may be necessary to cool the mixture obtained from stage (I), which is discharged from the column, before feeding into the reactor in stage (II).

In order to achieve the best possible mixing of alkyne, carbonyl compound and the at least one alkoxide present in the mixture from stage (I), the reaction mixture is stirred in stage (II). This stirring can in principle be carried out by any common method from the prior art. However, it is also conceivable to use a special type of introduction either to carry out the entire mixing process or to support the stirring.

In a preferred embodiment of the process according to the invention, the reaction mixture in stage (II) is mixed in a mixing device as described, for example, in DE-C 42 20 239, which is expressly incorporated into the present application in its full scope in this respect by way of reference. All suitable embodiments of the mixing device described therein are conceivable. Thus, for example, alkyne, carbonyl compound and the mixture from stage (I) can be introduced in separate streams into the mixing device, which accordingly must have at least three inlet apertures. Likewise, (a) alkyne and carbonyl compound or (b) alkyne and the mixture from stage (I) can be mixed before introduction into the mixing device, for example using a mixing device of the type described here, and the resultant mixture can be introduced into the mixing device as one stream and (a) the mixture from stage (I) or (b) the carbonyl compound or (c) the alkyne can be introduced into the mixing device as a further stream. Accordingly, the mixing device in this case must have at least two inlet apertures. For each of the embodiments, it is conceivable to divide the individual streams to be introduced into the mixing device into two or more streams before introduction by means of a suitable device installed upstream of the mixing device and for these two or more streams subsequently to be introduced into the mixing device.

Furthermore, two or more mixing devices of the type described here can be employed to mix the individual components which are reacted in stage (II). For example, mixtures can be prepared in each of these at least two mixing devices and subsequently combined.

If the components to be reacted in stage (II) are to be merely mixed with the aid of this mixing device, it should be ensured in the present invention that the reaction conditions in the mixing device, for example the temperature and pressure, are selected in such a way that no undesired reactions occur during the mixing process.

The mixing device is preferably employed as a reaction mixing pump. In the mixing device, the individual components to be reacted in stage (II) are both mixed and brought to reaction with one another, as described below.

It is in general conceivable in the present invention, for the reaction in stage (II) of alkyne with carbonyl compound and the mixture obtained from stage (I), to add one or more further suitable solvents in addition to the at least one organic solvent (L) and the at least one alcohol (A) present in the mixture obtained from stage (I).

Examples of suitable carbonyl compounds of the general structure R—CO—R' in the process according to the invention are aliphatic, araliphatic or heterocyclic ketones having up to 30 carbon atoms. R and R' here may be identical or different and may either be two separate radicals or may be bridged. It is likewise possible for the radicals R and/or R' to have olefinic or acetylenic functions. Examples which may be mentioned are acetone, isobutyl methyl ketone, 6,10-dimethyl-5-undecen-2-one, 6,11,14-trimethyl-2-pentadecanone, 2-methyl-2-hepten-6-one, 2-methylheptan-6-one, 4-(2,6,6-trimethyl-1-cyclohexanyl)-3-buten-2-one, methyl ethyl ketone, cyclohexanone, acetophenone, benzophenone and 4-piperidone, preference being given to acetone, isobutyl methyl ketone, 6,10-dimethyl-5-undecen-2-one, 6,11,14-trimethyl-2-pentadecanone, 2-methyl-2-hepten-6-one, 2-methylheptan-6-one and 4-(2,6,6-trimethyl-1-cyclohexenyl)-3-buten-2-one.

It is in principle also conceivable to use aldehydes containing no acidic hydrogen. Mention may be made here, inter alia, of aldehydes RCHO, where R=H or an alkyl radical having up to 30 carbon atoms. The preferred aldehyde is $CH_2O$.

Alkynes of the general structure R"—C≡C—H which may be mentioned are those in which R" is selected from the group consisting of hydrogen and an aliphatic, araliphatic or aromatic radical having up to 15 carbon atoms. Examples which may be mentioned are acetylene, propyne, 1-butyne, 1-pentyne, 1-hexyne, phenylacetylene, benzylacetylene, 3-methyl-1-butyne or compounds such as

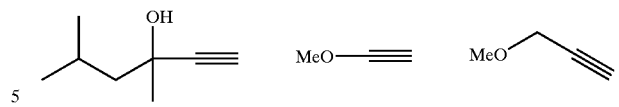

If the alkyne employed in the process according to the invention is acetylene, it is conceivable to prepare both alkynemonools and alkynediols by reaction with corresponding amounts of carbonyl compound and alkoxide. On use of an alkyne in which R"≠H, alkynemonools are produced.

It is of course also conceivable in the process according to the invention for the alkyne of the general structure R"—C≡C—H employed to be an alkynemonool and to prepare an alkynediol therefrom by reaction with the carbonyl compound and the alkoxide.

The alkyne of the general structure R"—C≡C—H used in the process according to the invention is preferably acetylene. The following alkynols, inter alia, can thus be prepared from the carbonyl compounds mentioned as preferred, where the term "alkynol" in principle covers all compounds which contain both at least one C—C triple bond and one or more hydroxyl groups: 2,5-dimethylhex-3-yne-2,5-diol (DMHDY), 3-methyl-3-hydroxybut-1-yne, 2,4,7,9-tetramethyl-4,7-dihydroxydec-5-yne, 3,7,11-trimethyl-6-dodecan-1-yn-3-ol, 3,7,11,15-tetramethyl-1-hexadecyn-3-ol, 3,7-dimethyloct-1-yn-6-en-3-ol, 3,7-dimethyloct-1-yn-3-ol, 1-penten-4-yn-3-ol, propynol, but-2-yn-1-ol, but-1-yn-3-ol or the compounds.

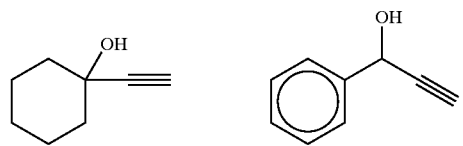

In the preparation of the unsaturated alcohol, the stoichiometric ratio between carbonyl compound and alkyne can essentially be selected as desired.

If, for example, alkynediols are prepared from the carbonyl compound and acetylene, a stoichiometric ratio between the carbonyl compound and acetylene is preferably selected in the range from 1.9:1 to 2.1:1, particularly preferably about 2:1. The stoichiometric ratio between the alkoxide and the carbonyl compound is preferably in the range from 0.9:1 to 2.1:1, particularly preferably in the range from 1:1 to 1.5:1 and in particular about 1.1:1.

If, for example, alkynemonools are prepared from the carbonyl compound and acetylene, the stoichiometric ratio between the carbonyl compound and acetylene is preferably selected in the range from 1:1 to 0.5:1, particularly preferably of about 0.6:1. The stoichiometric ratio between alkoxide and carbonyl compound is preferably in the range from 1:1 to 0.2:1 and in particular about 0.3:1.

The reaction temperature in the reaction of corresponding starting materials to give alkynediols in the process according to the invention is preferably in the range from 0 to 50° C., further preferably in the range from 10 to 40° C. and particularly preferably in the range from 25 to 35° C.

The reaction temperature in the reaction of corresponding starting materials to give alkynemonools in the process according to the invention is preferably in the range from 0 to 50° C., further preferably in the range from 0 to 35° C. and particularly preferably in the range from 0 to 20° C.

The pressures in said reactions in the case of the preparation of alkynemonools and alkynediols in the process according to the invention are preferably in the range from 1 to 20 bar, further preferably in the range from 1 to 5 bar and in particular 1 bar.

The yield of unsaturated alcohol (B) obtained in stage (II) in the process according to the present invention is preferably at least 75%, further preferably at least 80%, particularly preferably at least 85% and especially preferably at least 90%.

As already described above, the reaction in stage (II) is preferably carried out in a reaction mixing pump, as described in DE-C 42 20 239, where the design of the reaction mixing pump is not restricted to the mixing device disclosed therein. All conceivable designs of a device in which the starting materials in stage (II) can be both mixed and brought to reaction are likewise conceivable.

Ultimately, a mixture (G-II) comprising at least one unsaturated alcohol (B) as well as (A) and (L) is obtained in this stage (II).

Furthermore, alcohols present in the melt are preferably prepared in the process according to the invention by a process which comprises stages (I), (II), (II') and (III').

Since an alkynemonool and/or an alkynediol is formed in stage (II), depending on the choice of reaction partners, various hydrogenations are conceivable in stage (II') in the present process. If, for example, an alkynemonool or an alkynediol has been obtained, the alkynemonool or alkynediol can be hydrogenated in a partial hydrogenation to give the corresponding alkenol. However, it is also possible to prepare the respective alkanol by appropriate choice of the hydrogenation conditions.

The respective hydrogenation can in principle be carried out here by any suitable process according to the prior art. Thus, the respective hydrogenation can be carried out in one reactor or alternatively in a plurality of reactors connected in series. Each reactor can be operated in any conceivable mode, where mention should be made in particular of the trickle-bed and liquid-phase process in a fixed-bed reactor. In a preferred embodiment, the hydrogenation is carried out in two tubular reactors connected in series (fixed bed), the first of which is operated in trickle-bed mode with backmixing, and the second is operated in trickle-bed or liquid-phase mode with straight-through passage.

The hydrogenation can also be carried out in two or more reactors connected in parallel.

It is possible in this case for the components introduced into the one hydrogenation reactor or into the plurality of hydrogenation reactors to be pre-heated or alternatively pre-cooled before the introduction. This can take place, for example, in one or more heat exchangers.

It is furthermore conceivable to regulate the temperature of the hydrogenation reactor or hydrogenation reactors itself or themselves, which can be carried out in all processes of the prior art. It is thus possible, for example, to compensate for falling hydrogenation activity of the at least one catalyst employed for the hydrogenation, as described below, by increasing the reactor temperature. This increase in the reactor temperature can be carried out, for example, in an exothermic hydrogenation reaction by cooling the reactor. It is of course also conceivable actively to increase the reactor temperature by external heating.

If an alkynol is hydrogenated to an alkenol in the process according to the invention, any suitable catalyst known from the prior art can be employed for this purpose. Possible catalysts here include, for example, Pd or Pd/Pb on $CaCO_3$ (Lindlar catalyst). If desired, the catalysts, for example Pd, can be partially poisoned, for example by CO, in order to achieve good selectivities.

If an alkynol is hydrogenated to an alkanol in the process according to the invention, any suitable catalyst known from the prior art can be used for this purpose. Examples of known catalysts are Pd, Pt, Ni (also Raney nickel), Co, Ru or Rh catalysts, which can be employed as supported or unsupported catalysts. The supports used here can be any suitable common support, for example $Al_2O_3$, $SiO_2$ or C.

In a preferred embodiment of the process in which one or more alkynols are hydrogenated to the corresponding alkanols, the catalysts used are supported catalysts or unsupported catalysts. Active hydrogenation metals which may be mentioned here are especially the metals from sub-groups 1, 7 and 8 of the Periodic Table. Preference is given here to Ni, Ru, Pd, Pt and Rh.

In a particularly preferred embodiment of the hydrogenation of alkynols to alkanols, the catalyst used in the process according to the invention is a supported Pd catalyst, where the support material comprises aluminum oxide.

The hydrogenation of the alkynols to the respective alkanols is carried out in the process according to the invention at pressures of, in general, from b 1to 300 bar, preferably from 10 to 200 bar, particularly preferably from 15 to 100 bar and especially preferably from 20 to 50 bar.

In general, the temperatures in the hydrogenation in the process according to the invention in the case of the hydrogenation of alkynols to the respective alkanols are in the range from 30 to 250° C., preferably in the range from 50 to 200° C. and particularly preferably in the range from 80 to 160° C.

If alkynols are hydrogenated to the respective alkenols in the process according to the invention, the temperatures during the hydrogenation are generally in the range from 30 to 200° C., preferably in the range from 40 to 150° C. and especially preferably in the range from 50 to 130° C.

If two or more reactors connected in series are employed in the hydrogenation in the process according to the invention, it is conceivable to set different pressures and/or different temperatures for the hydrogenation in the individual reactors. Thus, it is possible, inter alia, not to regulate the temperature of a product stream from a first reactor, which, owing to heat of reaction being liberated, has a higher temperature than the starting-material stream into this first reactor, before introduction into a second reactor. However, it is of course also possible to cool the product stream from the first reactor before introduction into the second reactor via intermediate cooling provided between these two reactors. Thus, it is possible, for example, to match the hydrogenation temperature in the second reactor individually to the activity of the catalyst used therein.

It is of course also conceivable to prepare a mixture of alkenol and alkanol from the alkynol. This is possible, for example, through an appropriate choice of the hydrogenation conditions. A further possibility for this purpose comprises dividing the product stream from stage (II), which consists of the mixture obtained in stage (II), into two or more streams and to hydrogenate each stream in separate reactors, in which case the hydrogenation conditions in each reactor may be different and thus alkenols and alkanols can be prepared from the alkynol in a simple manner.

Depending on the hydrogenation conditions, the following alkenols and/or alkanols can be prepared from the above-described alkynols preferably prepared: 2,5-dimethylhexane-2,5-diol (DMHD), 3-methyl-3-hydroxy-but-1-ene, 2-methyl-2-hydroxybutane, 3,7,11-trimethyl-3-hydroxy-1,6-dodecadiene, 3,7,11,15-tetramethylhexadec-1-en-3-ol, 3,7-dimethyl-1,6-octadien-3-ol, 3,7-dimethyloct-1-en-3-ol, 3-methyl-1-(2,6,6-trimethyl-1-cyclohexen-1-ol), 1,4-pentadien-3-ol and 3-methyl-1-(2,6,6-trimethyl-1-cyclohexen-1-ol).

Stage (II') is not restricted to hydrogenation of the triple bond of the at least one alkynol obtained from stage (II). Depending on the chemical structure of the at least one alkyne employed in stage (II) and/or of the at least one carbonyl compound, it is conceivable for the radicals R and/or R' and/or R" to be chemically modified in stage (II') by carrying out, for example, reactions on functional groups present in these radicals. It is furthermore also conceivable in the process according to the invention for such reactions to be carried out in addition to the hydrogenations described above.

In a further preferred embodiment of the process according to the invention, stage (II), as described above, is carried out in individual steps (aa) to (ff). Accordingly, the present invention also describes a process, as described above, in which stage (II) comprises the following steps (aa) to (ff):

(aa) reaction of at least one carbonyl compound of the general structure R—CO—R' with at least one alkyne of the general structure R"—C≡C—H and the mixture (G-I) obtained in stage (I) to give a mixture (M-aa);

(bb) hydrolysis of the mixture (M-aa) obtained from step (aa) to give a multiphase mixture (M-bb) comprising at least one organic phase;

(cc) removal of the at least one organic phase from the multiphase mixture (M-bb) obtained in step (bb);

(dd) extraction of the at least one organic phase removed in step (cc);

(ee) neutralization of the at least one organic phase extracted in step (dd) to give a mixture (M-ee) comprising at least one alkali or alkaline earth metal salt;

(ff) removal of the at least one alkali or alkaline earth metal salt from the mixture (M-ee) obtained in step (ee) to give a mixture (G-II) comprising at least the alcohol (A), the solvent (L) and an unsaturated alcohol (B).

The reaction of the at least one carbonyl compound with the at least one alkyne and the mixture (G-I) obtained in stage (I), as described above, firstly gives a mixture (M-aa), which is fed to step (bb). In this step (bb), the at least one unsaturated alcohol (B) is liberated by hydrolysis.

There are in principle no restrictions to the manner of carrying out the hydrolysis. Thus, for example, it can be carried out in one or more reactors, it being possible, if desired, for the temperature in the respective reactor to be regulated. Cooling by brine, for example, is conceivable. Also conceivable is cooling of the hydrolysis water, which can likewise be carried out by any conceivable method of the prior art. In general, the reaction mixture is stirred during performance of the hydrolysis, which can take place by any common method of the prior art. For example, the stirring and mixing can be carried out using a mixing device as described above and disclosed, for example, in DE-C 42 20 239.

The aqueous phase employed for this hydrolytic step (bb) results, in a particularly preferred embodiment of the process according to the invention, from the extraction in step (dd). Naturally, further water can also be added in addition. Both the water used for the hydrolysis and the reaction mixture to be hydrolyzed can be brought to the desired temperature before introduction into the at least one hydrolysis reactor, which can be carried out, for example, by heat exchangers.

The hydrolysis in step (bb) gives a mixture (M-bb) consisting of at least two phases, namely at least one organic phase and at least one aqueous phase. The at least one organic phase is separated off from this mixture (M-bb) in step (cc). This phase separation can in principle be carried out by any common method. It is conceivable here, in the case of two or more organic phases, to separate these off together as a multiphase organic mixture or as two or more separate organic phases. It is likewise conceivable, in the case of two or more aqueous phases, to separate these off together as a multiphase aqueous mixture or as two or more separate aqueous phases.

In a preferred embodiment of the present invention, the hydrolyzed mixture (M-bb) from step (bb) is fed into one or more phase-separation vessels, which may be designed in such a way that the temperature of the multiphase mixture to be separated can be regulated in the separation vessel. The phase separation is preferably carried out at temperatures which are generally in the range from 10 to 80° C., preferably in the range from 20 to 60° C. and particularly preferably in the region of 40° C.

In a particularly preferred embodiment of the process according to the invention, the at least one aqueous phase, which has a content of alkali and/or alkaline earth metal hydroxide in the range from 2 to 60% by weight, preferably in the range from 30 to 35% by weight, is recycled into stage (I) as starting material. In order, in the alkoxide preparation taking place in stage (I), to achieve a base concentration which enables the preparation of the at least one alkoxide (AL), it may be necessary in stage (I) to add a further aqueous solution comprising alkali and/or alkaline earth metal hydroxide in addition to the at least one aqueous phase comprising aqueous alkali and/or alkaline earth metal hydroxide obtained from step (cc).

The at least one organic phase is extracted in a next step (dd). If a single organic phase or a mixture of a plurality of organic phases was separated off in step (cc), this phase or this mixture is extracted. If a plurality of organic phases was separated off, it is conceivable, for example, to extract each individual organic phase separately.

In a preferred embodiment of the present invention, the extraction is carried out using the aqueous phase obtained from stage (I) by distillation. It is of course conceivable here additionally to add water to this aqueous phase.

The extraction can be carried out by any possible method known from the prior art. Mention may be made here, inter alia, of the use of columns, such as perforated-plate columns, pulsed elevated-plate columns or packed columns. In the preferred embodiment, the extraction is carried out in countercurrent, with the temperature of the extraction mixture during the extraction generally being in the range from 30 to 50° C., preferably approximately 40° C.

In this extraction step (dd), the at least one alkali or alkaline earth metal hydroxide is withdrawn from the at least one organic phase to the extent that the alkali and/or alkaline earth metal hydroxide content of the at least one organic phase is less than 1% by weight, preferably less than 0.1% by weight and particularly preferably less than 0.01% by weight.

The aqueous phase which results from the extraction is, in a preferred embodiment of the present process according to the invention, recycled into step (bb).

The at least one extracted organic phase can be neutralized in a further step (ee). The neutralization here is carried out by adding acid, acids which may be mentioned being, inter alia, phosphoric acid, formic acid, acetic acid, sulfuric acid and carbonic acid. It is likewise conceivable to use extremely fine carbon dioxide. The process according to the invention is preferably carried out using phosphoric acid.

In the subsequent step (ff), the at least one alkali or alkaline earth metal salt formed in the neutralization is removed from the mixture (M-ee) obtained from step (ee). This removal can in general be carried out by any method known from the prior art. The salt removal can be omitted in the process according to the invention if the product from which salt is removed is not subjected to especially high temperatures. This is the case, for example, if the at least one unsaturated alcohol (B) is not hydrogenated.

In a preferred embodiment of the process according to the invention, the removal of the at least one alkali or alkaline earth metal salt from the mixture (M-ee) obtained in step (ee) is carried out by total evaporation of the organic substances using, for example, a thin-film evaporator or a falling-film evaporator. The at least one alkali or alkaline earth metal salt remaining is rinsed out of the evaporator by means of one or more suitable substances. Substances which are suitable for this purpose are, inter alia, polyalkylene glycols, for example polyethylene glycol. In a particularly preferred embodiment, a proportion of at least 0.5%, preferably from 1 to 2% and particularly preferably at least 1 to 10% of the substances employed to rinse out the at least one alkali or alkaline earth metal salt is recycled.

If the at least one unsaturated alcohol (B) should not be hydrogenated in the process according to the invention or if the at least one hydrogenated alcohol (C) is not sufficiently thermally stable, so that loss of valuable product occurs at the temperatures arising during total evaporation, the salt removal can also be carried out via ion exchange. With respect to ion exchange, all suitable methods which are known from the prior art are conceivable.

In a further preferred embodiment, the high-boiling bottom product from the distillation in stage (III) is fed into the evaporator in addition to the mixture (M-ee) obtained from step (ee). The result of this is that residues of valuable product present in the high-boiling bottom product are recycled into the process. A further advantage associated with this recycling is the fact that the high-boiling bottom product mentioned acts as lubricant for the evaporator.

The evaporator distillate resulting from the total evaporation of the organic substances is condensed in the process according to the invention. In a preferred embodiment of the process according to the invention, this condensation is carried out in at least two steps, in a further preferred embodiment in two steps. The temperature at which the first condensation step is carried out is generally in the range from 30 to 80° C., preferably in the range from 35 to 50° C. and further preferably about 40° C. The temperature at which the second condensation step is carried out is generally in the range from 0 to 40° C., preferably in the range from 5 to 20° C. and further preferably about 10° C.

The mixture (G-II) which is formed after the condensation steps and which comprises the at least one unsaturated alcohol (B), (L) and (A) is then fed to stage (II') or (III). It is conceivable here that, in the case of a plurality of condensation steps, only the condensate from a condensation step in stage (II') and/or (III) is processed further. However, it is also possible for a plurality of condensation streams to be further processed together in stage (II') and/or (III).

In stage (III) or (III') of the present invention, the mixture (G-II) or (G-II') obtained from the preceding stage is distilled, giving the at least one alcohol (B) or (C) prepared in the preceding stage. Likewise, the at least one organic solvent (L) and the at least one alcohol (A) is also removed. This distillation can in turn be carried out by any common method known from the prior art. In the preferred embodiment of the process according to the invention, the distillation is carried out in a packed column with dividing wall.

The (L) and (A) obtained after the distillation in stage (III) or (III') are, in accordance with the process according to the invention, recycled into stage (I) as starting materials, where (L) and (A) can be recycled into stage (I) separately from one another or as a mixture.

Each of stages (I), (II), (II'), (III) and (III') and each of steps (aa) to (ff) can in principle be carried out continuously or batchwise. In a preferred embodiment of the process according to the invention, these stages and steps are designed in such a way that each stage and each step can be carried out continuously.

In a preferred embodiment of the process according to the invention, the at least one unsaturated alcohol (B) or the at least one alcohol (C) is obtained in stage (III) or stage (III') as a molten product during the distillation. This product can be shaped directly to give droplets after the distillation. The shaping of the droplets is per se naturally a discontinuous process. Since the feed of melt for droplet formation preferably takes place continuously and the shaped droplets deposited on the cooling surface are preferably transported off the cooling surface continuously as tablet-shaped granular material, the overall process is, however, preferably a continuous process.

Accordingly, the present invention also describes a process as described above in which each stage and each step is carried out as a continuous process.

The present invention also describes, in particular, an integrated process for the preparation of a molten unsaturated alcohol (B) and the production of a tablet-shaped granular material from this melt which comprises the following steps (aaa) to (jjj) carried out continuously:

(aaa) reaction of at least one alkali or alkaline earth metal hydroxide with at least one alcohol (A) in at least one organic solvent (L) using the aqueous phase (P-ddd) obtained in step (ddd) to give a mixture (G-aaa) comprising at least the solvent (L), the alcohol (A) and an alkoxide (AL), and an aqueous phase (P-aaa), which is fed to step (eee);

(bbb) reaction of at least one carbonyl compound of the general structure R—CO—R' with at least one alkyne of the general structure R"—C≡C—H and the mixture (G-aaa) obtained in step (aaa) to give a mixture (G-bbb) comprising at least one unsaturated alcohol (B);

(ccc) hydrolysis of the mixture (G-bbb) from step (bbb) using the aqueous phase (P-eee) obtained in step (eee) to give a multiphase mixture (M-ccc) comprising at least one organic phase and at least one aqueous phase;

(ddd) removal of the at least one organic phase from the multiphase mixture (M-ccc) obtained in step (ccc) to give at least one aqueous phase (P-ddd), which is recycled into step (aaa);

(eee) countercurrent extraction of the at least one organic phase removed in step (ddd) using the aqueous phase (P-aaa) obtained in step (aaa) to give an aqueous phase (P-eee), which is recycled into step (ccc);

(fff) neutralization of the at least one organic phase obtained in step (eee) to give a mixture (G-fff) comprising at least one alkali or alkaline earth metal salt, and at least the alcohol (A), the solvent (L) and the at least one unsaturated alcohol (B);

(ggg) removal of the at least one alkali or alkaline earth metal salt from the mixture (G-fff) obtained in step (fff) to give a mixture (G-ggg) comprising at least the alcohol (A), the solvent (L) and the at least one unsaturated alcohol (B);

(hhh) distillation of the mixture (G-ggg) obtained in step (ggg) to give the at least one unsaturated alcohol (B) in molten form, a mixture (M-hhh) comprising the solvent (L) and the alcohol (A), and a mixture (G-hhh) containing small amounts of the at least one unsaturated alcohol (B), where the solvent (L) and the alcohol (A) are recycled into step (aaa) as a mixture, and the mixture (G-hhh) containing small amounts of the at least one unsaturated alcohol (B) is recycled into step (ggg), and (jjj) production of tablet-shaped granular material from the melt obtained in (hhh), which comprises the at least one unsaturated alcohol (B).

In addition, the present invention also describes an integrated process for the preparation of at least one hydrogenated alcohol (C) which comprises the steps (aaa) to (ggg), which are carried out continuously, as described above, and the steps (ggg'), (hhh') and (jjj'), which are carried out continuously after step (ggg):

(ggg') hydrogenation of the at least one unsaturated alcohol (B) in the mixture (G-ggg) obtained in step (ggg) to give a mixture (G-ggg') comprising at least the alcohol (A), the solvent (L) and at least one hydrogenated alcohol (C);

(hhh') distillation of the mixture (G-ggg') obtained in step (ggg') to give the at least one hydrogenated alcohol (C) in molten form, a mixture (M-hhh') comprising the solvent (L) and the alcohol (A), and a mixture (G-hhh') containing small amounts of the at least one hydrogenated alcohol (C), where the solvent (L) and the alcohol (A) are recycled into step (aaa) as a mixture, and the mixture (G-hhh') containing small amounts of the at least one hydrogenated alcohol (C) is recycled into step (ggg), (jjj') production of tablet-shaped granular material from the melt obtained in (hhh'), which comprises the at least one saturated alcohol (C).

It is of course also conceivable for the alcohols (B) and (C) preferably formed in molten form in stages (III) and (III') not to be shaped to give droplets directly thereafter. In this case, the melt can, for example, be collected and shaped to droplets at a later time. It is also conceivable here for the melt to be allowed to solidify during storage and to be liquefied again before shaping to droplets. However, it is likewise conceivable to keep the melt in the liquid state during storage.

It is furthermore conceivable for the at least one unsaturated alcohol (B) or the at least one saturated alcohol (C) not to be formed in molten form in step (hhh) or in step (hhh'). In this case, (B) or (C) are first converted into a melt, and the melt is subsequently shaped to droplets. Any suitable method is conceivable here for the preparation of the melt of (B) or (C).

As described in detail above, the present invention provides a process for the production of tablet-shaped granular material in which a large number of products resulting from the individual stages and steps are recycled back into the process. A cost-saving and ecologically efficient process is thus provided, which is further improved by the preferred continuous operation of each stage and each step.

Particularly preferred alcohols present in the melt in the process according to the invention include polyalkylene glycols, for example polyethylene glycols, polypropylene glycols or trimethylolpropane. Preference is likewise given to cyclohexanols, for example 1-ethynyl-1-cyclohexanol, hexanediols, for example 1,6-hexanediol, butynediols, for example 2-butyne-1,4-diol, hexynediols, for example 3-hexyne-2,5-diol, and neopentyl glycol.

In a further preferred embodiment, the present invention relates to a process as described above wherein the alcohol is selected from the group consisting of dimethylhexynediol, dimethylhexanediol, neopentyl glycol and trimethylolpropane.

Regarding DMHD, it is in particular conceivable for this compound to be prepared in a process comprising stages (I), (II), (II') and (III). In particular, it is furthermore conceivable for dimethylhexanediol to be prepared by hydrogenation of dimethylhexynediol (DMHDY), which is itself prepared by a process comprising stages (I), (II) and (III).

It is of course also possible to prepare DMHD by any other possible process. Thus, for example, it is conceivable to prepare DMHD by a free-radical reaction. In this reaction, for example, methylbutynol and methylbutenol and isopropanol are reacted with one another with addition of a free-radical initiator, for example dibutyl peroxide.

In a preferred embodiment of the process according to the invention, the melt, which comprises at least one alcohol, as described above, is shaped to droplets in such a way that pre-crystallization does not occur.

For the purposes of the present invention, the term "pre-crystallization" is taken to mean one or more process steps in which, after production of the melt, the crystal content of the melt is generated or increased by addition of crystals to the melt or by using a crystallization device, in general cooling surfaces equipped with wipers and scrapers, as described, for example, in the two abovementioned publications, or by partial evaporation of the melt or a solution.

Accordingly, the present invention also relates to a process as described above wherein the melt is not subjected to pre-crystallization before deposition of the droplets.

The melt which is shaped to give droplets can have essentially any desired crystal content so long as it is ensured that the melt can be shaped to give droplets and deposited on the cooling surface. In a preferred embodiment of the process according to the invention, a tablet-shaped granular material is produced here, where the melt has a crystal content of less than 3% by weight, in particular less than 2% by weight, particularly preferably less than 1% by weight, in each case based on the total weight of the melt, and very particularly preferably contains no crystals.

The present invention therefore also relates to a process as described above wherein the melt has a crystal content of less than 3% by weight.

In general, the process according to the invention is suitable for converting melts of essentially any viscosity into granular material so long as it is ensured that the melt can be shaped to give droplets and deposited on the cooling surface. The process according to the invention is preferably used for the conversion of melts having a viscosity in the range from 1 to 1000 mPas, preferably in the range from 1 to 100 mPas, particularly in the range from 1 to 20 mPas, into granular material.

The present invention therefore also relates to a process as described above wherein the melt has a viscosity in the range from 1 to 1000 mPas.

In a further preferred embodiment of the process according to the invention, the melt which is shaped to give droplets is deposited on a cooling surface which is poorly wettable by the melt.

The material of the cooling surface which is poorly wettable by the melt shaped to give droplets can be selected essentially freely in the present invention and can be selected in accordance with the respective composition of the melt which is to be converted into granular material. It should of course be ensured here that the material of the cooling surface is chemically inert to the respective melt and does not hinder the requisite cooling of the cooling surface. Under these prerequisites, essentially all suitable materials known from the prior art can be employed. In a preferred embodiment, the material of the cooling surface on which the droplets are deposited is made of metal, further preferably of steel and very particularly preferably of stainless steel.

The present invention therefore also relates to a process as described above wherein the cooling surface on which the droplets are deposited in (iii) is made of stainless steel.

Through the specific choice according to the invention of the material of the cooling surface, it can be achieved in a simple manner that the melt shaped to give droplets only spreads a little, or not at all, on the cooling surface before the melt solidifies to give a granular material. In this way, it is possible to omit, in particular, devices and processes which have to influence the properties of the melt in order to be able to control the shape of the granular material. In particular, pre-crystallization of the melt is, as described above, unnecessary in the process according to the invention.

As far as the shaping of the melt to give droplets is concerned, any suitable methods and devices are conceivable in the process according to the invention.

In particular, mention should be made of devices in which the melt is discharged in the form of droplets by means of pressure in cycles via valves or slides or via openings which are opened in cycles or in which the melt is discharged in the form of droplets or pressed out by oscillating or rotating displacement elements.

In a preferred embodiment of the present invention, a melt is, for example, introduced into a container which has an outlet aperture through which the melt can exit and be passed to a valve, which is regulated in such a way that the melt is deposited dropwise on the cooling surface beneath. The droplet production here can be controlled, for example, by the valve being opened in cycles. Both the container per se and the lines, if present, and the valve itself may be heated in order to be able to control the temperature of the melt correspondingly. It is conceivable here, inter alia, for the melt overall to have the same temperature. However, it is likewise also possible for the container, lines, if present, and the valve to be held at different temperatures.

Further devices for forming droplets from the melt are described, for example, in DE-C 34 21 625, DE-C 29 41 802 and DE-B 28 53 054, which in this respect are incorporated into the contents of the present invention by way of reference.

In the process according to the invention, preferred devices for droplet formation are those which have a plurality of droplet discharge points for simultaneous production of a plurality of droplets.

In the production of the granular material from the melt by the process according to the invention, essentially any suitable temperatures can be selected for the melt. The same applies to the temperatures of the cooling surface.

Particularly preferred application temperatures of the melt are generally in the range up to 100° C., preferably in the range up to 30° C. and particularly preferably in the range up to 15° C. above the melting point of the melt.

The present invention also relates to a process as described above wherein the temperature of the melt shaped to give droplets on application to the cooling surface is up to 100° C. above the melting point of the melt.

The temperature of the cooling surface on which the melt shaped to give droplets is deposited is generally selected in such a way that the melt cools at the desired rate.

In general, these temperatures of the cooling surface are in the range from −30 to +80° C., preferably in the range from 0 to +50° C. and particularly preferably in the range from +15 to +40° C.

The present invention therefore also relates to a process as described above wherein the cooling surface on which the melt shaped to give droplets is deposited has a temperature in the range from −30 to +80° C.

In accordance with the process according to the invention, tablet-shaped granular material having different geometries can be produced depending, inter alia, on the temperature of the melt during deposition of the droplets, the droplet shape, the droplet volume and the temperature of the cooling surface. By variation, inter alia, of the abovementioned parameters, the height and diameter, for example, of the tablets can be matched to the requirements of the further use.

In general, the mean diameter of the granular material produced by the process according to the invention is in the range from 1 to 20 mm, preferably in the range from 3 to 10 mm and particularly preferably in the range from 4 to 8 mm. The mean height of the granular material produced by the process according to the invention is generally in the range from 0.5 to 5 mm, preferably in the range from 1 to 4 mm and particularly preferably in the range from 1.5 to 3 mm.

The present invention therefore also relates to a granular material as described above which has a mean diameter in the range from 1 to 20 mm and a mean height in the range from 0.5 to 5 mm.

In a very particularly preferred embodiment, tablet-shaped granular materials are produced which essentially consist of DMHD or DMHDY or neopentyl glycol or trimethylolpropane. In general, the DMHD or DMHDY or neopentyl glycol or trimethylolpropane content of the tablet-shaped granular material in this case is greater than 90% by weight, preferably greater than 95% by weight and particularly preferably greater than 99% by weight, in each case based on the total weight of the granular material.

The present invention therefore also relates to a granular material as described above which consists of greater than 90% by weight, based on the total weight of the granular material, of dimethylhexynediol or dimethylhexanediol or neopentyl glycol or trimethylolpropane.

A particular advantage of the granular material according to the invention is that, compared with, for example, flake-shaped granular material, it has a low tendency toward compaction or crust formation. However, products having a high tendency toward compaction or crust formation are, inter alia, more difficult to handle and have poor storage properties.

The present invention therefore also relates to a granular material as described above which has a low tendency toward compaction.

Compared with, for example, flake-shaped granular material, the tablet-shaped granular material according to the invention also has a reduced dust content. For the purposes of the present invention, "dust" is taken to mean particles which have the same composition as the granular material, but have a size which is below that of the granular material and which is undesired for handling and use of the granular material.

The invention is illustrated below by a working example.

EXAMPLE

A DMHD melt having a purity of 99.85%, determined as area percent from gas-chromatographic analysis, was introduced into a 1l flask without pressure at a temperature of 102° C. under a blanket of nitrogen. The flask was fitted with a double jacket for temperature control of the melt and its temperature was controlled correspondingly. An outlet tube provided with a fine regulation valve, both of which were likewise heated, was located at the base of the flask.

By opening the valve in cycles, the melt was discharged in the form of droplets. The droplet discharge point was 10 mm above the cooling surface used for solidification of the droplets. The cooling surface consisted of stainless steel and was set to a temperature of 25° C. by means of cooling water. The droplets were deposited on the cooling surface one after the other. Solidification gave tablets which had a diameter of from 5 to 7 mm and a thickness of from 1.8 to 2.7 mm.

The same DMHD melt was applied to a cooling roll for the production of flakes. The cooling roll had a diameter of 200 mm and a width of 100 mm.

The roll was immersed into a melt trough containing the DMHD melt at a temperature of 110° C. The cooling roll was cooled to a temperature of 25° C. by means of cooling water. At a roll speed of 2 rpm, the melt was drawn onto the roll, solidified and, after solidification, scraped off by a device. The flakes formed had a thickness of from 0.6 to 0.7 mm and an irregular size of from a few square millimeters to approximately fingernail size. In contrast to the tablet-shaped granular product, the flake product had a significant dust content with particles <1 mm.

The flakes and tablets obtained were investigated for caking behavior in a comparative test. To this end, in each case 30 g of flakes and tablets were introduced into cylindrical metal vessels (internal diameter 43 mm, height 50 mm).

After leveling of the pile cone, the samples in the metal vessels were weighted from above using metal plungers (weight 455 g each). The weighted samples were left to stand for 14 days at room temperature (ambient air in the laboratory). After expiry of the storage time, the plungers were removed and the degree of compaction of the flakes or tablets was tested by rotating the cylindrical vessels and recording the proportion of the flakes or tablets which flowed out of their own accord. The results shown in Table 1 below were achieved:

TABLE 1

| Sample number | Fraction flowing out/% by wt. |
|---|---|
| Tablets No. 1 | 24 |
| Tablets No. 2 | 17 |
| Tablets No. 3 | 32 |
| Flakes No. 1 | 1.9 |
| Flakes No. 2 | 0.7 |
| Flakes No. 3 | 1.6 |

In addition, it was observed that the fraction of the tablets which did not flow out freely did flow out as dispersed granular material when the cylindrical vessel was just tapped gently, while the flakes only flowed out when tapped more strongly and then as a substantially coherent agglomerate.

We claim:
1. A process for the production of tablet-shaped granular material from a melt, in which
   (i) a melt is prepared,
   (ii) the prepared melt is shaped to droplets,
   (iii) the droplets are deposited on a cooling surface, and
   (iv) the deposited droplets solidify to give the granular material, wherein the melt comprises an alcohol, and the melt has a melting point of 30° C. or above.

2. A process as claimed in claim 1, wherein the alcohol is selected from the group consisting of
   (a) an alcohol (B) which is provided by a process which comprises the following stages (I) to (III):
      (I) reaction of at leats one alkali or alkaline earth metal hydroxide with at least one alcohol (A) in at least one organic solvent (L) to give a mixture (G-I) comprising at least the alcohol (A), the solvent (L) and an alkoxide (AL);
      (II) reaction of at least one carbonyl compound of the general structure R—CO—R' with at leat one alkyne of the general structure R"—C≡X—H and the mixture (G-I) obtained in stage (I) to give a mixture (G-II) comprising at least the alcohol (A), the solvent (L) and an unsaturated alcohol (B);
      (III) distillation of the mixture (G-II) obtained in stage (II) to give the at least one alcohol (B) and a mixture (G-III) comprising the solvent (L) and the alcohol (A),
      where the solvent (L) obtained in stage (III) and the alcohol (A) obtained in stage (III) are recycled into stage (I) as a mixture,
   (b) an alcohol (C) which is prepared by a process which comprises the following stages (I) to (III'):
      (I) reaction of at least one alkali or alkaline earth metal hydroxide with at least one alcohol (A) in at least one organic solvent (L) to give a mixture (G-I) comprising at least the alcohol (A), the solvent (L) and an alkoxide (AL);
      (II) reaction of at least one carbonyl compound of the general structure R—CO—R' with at least one alkyne of the general structure R"—C≡C—H and the mixture (G-I) obtained in stage (I) to give a mixture (G-II) comprising at least the alcohol (A), the solvent (L) and an unsaturated alcohol (B);
      (II') hydrogenation of at least one unsaturated alcohol (B) in the mixture (G-II) obtained from stage (II) to give a mixture (G-II') comprising at least one hydrogenated alcohol (C), the alcohol (A) and the solvent (L);
      (III') distillation of the mixture (G-II') obtained in stage (II') to give the at least one alcohol (C) and a mixture (G-III') comprising the solvent (L) and the alcohol (A),
      where the solvent (L) obtained in stage (III') and the alcohol (A) obtained in stage (III') are recycled into stage (I) as a mixture, and
   (c) a mixture of two or more thereof.

3. A process as claimed in claim 2, wherein the alcohol is selected from the group consisting of dimethylhexynediol, dimethylhexanediol, neopentyl glycol and trimethylolpropane.

4. A process as claimed in claim 3, wherein the melt has at least one property selected from the group comprising:
   (i) the melt is not subjected to pre-crystallization before deposition of the droplets,
   (ii) the melt has a crystal content of less than 3% by weight, and
   (iii) the melt has a viscosity in the range from 1 to 1000 mPas.

5. A process as claimed in claim 2, wherein the melt has at least one property selected from the group comprising:
   (i) the melt is not subjected to pre-crystallization before deposition of the droplets,
   (ii) the melt has a crystal content of less than 3% by weight, and (iii) the melt has a viscosity in the range from 1 to 1000 mPas.

6. A process as claimed in claim 1, wherein the melt has at least one property selected from the group comprising:

(i) the melt is not subjected to pre-crystallization before deposition of the droplets, (ii) the melt has a crystal content of less than 3% by weight, and (iii) the melt has a viscosity in the range from 1 to 1000 mPas.

7. A process as claimed in claim 1, wherein the cooling surface on which the droplets are deposited in (iii) is made of stainless steel.

8. A process as claimed in claim 1, wherein the temperature of the melt shaped to give droplets on application to the cooling surface is up to 100° C. above the melting point of the melt.

9. A process as claimed in claim 1, wherein the cooling surface on which the melt shaped to give droplets is deposited has a temperature in the range from −30 to +80° C.

10. A tablet-shaped granular material which can be produced by a process in which (i) a melt is prepared, (ii) the prepared melt is shaped to droplets, (iii) the droplets are deposited on a cooling surface, and (iv) the deposited droplets solidify to give the granular material, wherein the melt has a melting point of 30° C. or above and wherein the melt comprises an alcohol that is selected from the group consisting of:

(a) an alcohol (B) which is prepared by a process which comprises the following stages (I) to (III):

(I) reaction of at least one alkali or alkaline earth metal hydroxide with at least one alcohol (A) in at least one organic solvent (L) to give a mixture (G-I) comprising at least the alcohol (A), the solvent (L) and an alkoxide (AL);

(II) reaction of at least one carbonyl compound of the general structure R—CO—R' with at least one alkyne of the general structure R"—C≡C—H and the mixture (G-I) obtained in stage (I) to give a mixture (G-II) comprising at least the alcohol (A), the solvent (L) and an unsaturated alcohol (B);

(III) distillation of the mixture (G-II) obtained in stage (II) to give the at least one alcohol (B) and a mixture (G-III) comprising the solvent (L) and the alcohol (A), where the solvent (L) obtained in stage (III) and the alcohol (A) obtained in stage (III) are recycled into stage (I) as a mixture, (b) an alcohol (C) which is prepared by a process which comprises the following stages (I) to (III'):

(I) reaction of at least one alkali or alkaline earth metal hydroxide with at least one alcohol (A) in at least one organic solvent (L) to give a mixture (G-I) comprising at least the alcohol (A), the solvent (L) and an alkoxide (AL);

(II) reaction of at least one carbonyl compound of the general structure R—CO—R' with at least one alkyne of the general structure R"—C≡C—H and the mixture (G-I) obtained in stage (I) to give a mixture (G-II) comprising at least the alcohol (A), the solvent (L) and an unsaturated alcohol (B);

(II') hydrogenation of at least one unsaturated alcohol (B) in the mixture (G-II) obtained from stage (II) to give a mixture (G-II') comprising at least one hydrogenated alcohol (C), the alcohol (A) and the solvent (L);

(III') distillation of the mixture (G-II') to give the at least one alcohol (C) and a mixture (G-III') comprising the solvent (L) and the alcohol (A), where the solvent (L) obtained in stage (III') and the alcohol (A) obtained in stage (III') are recycled into stage (I) as a mixture, and (c) a mixture of two or more thereof.

11. A granular material as claimed in claim 10, which has a mean diameter in the range from 1 to 20 mm and a mean height in the range from 0.5 to 5 mm.

12. A granular material as claimed in claim 11, which comprises more than 90% by weight, based on the total weight of the granular material, of dimethylhexynediol or dimethylhexanediol or neopentyl glycol or trimethyolpropane.

13. A granular material as claimed in claim 10, which comprises more than 90% by weight, based on the total weight of the granular material, of dimethylhexynediol or dimethylhexanediol or neopentyl glycol or trimethyolpropane.

14. A granular material as claimed in claim 10, which has a low tendency toward compaction.

* * * * *

UNITED STATES PATENT AND TRADEMARK OFFICE
CERTIFICATE OF CORRECTION

PATENT NO.   : 6,638,619 B1
DATED        : October 28, 2003
INVENTOR(S)  : Brunner et al.

It is certified that error appears in the above-identified patent and that said Letters Patent is hereby corrected as shown below:

<u>Column 18,</u>
Line 5, "leats" should be -- least --;
Line 11, "leat" should be -- least --.

Signed and Sealed this

Ninth Day of December, 2003

JAMES E. ROGAN
*Director of the United States Patent and Trademark Office*